US011925625B2

(12) United States Patent
Matsuda et al.

(10) Patent No.: US 11,925,625 B2
(45) Date of Patent: Mar. 12, 2024

(54) METHODS OF TREATING CHEMICAL GAS EXPOSURE

(71) Applicant: MediciNova, Inc., La Jolla, CA (US)

(72) Inventors: Kazuko Matsuda, La Jolla, CA (US); Federico Carlos Aréjola Gaeta, Málaga (ES)

(73) Assignee: MediciNova, Inc., La Jolla, CA (US)

( * ) Notice: Subject to any disclaimer, the term of this patent is extended or adjusted under 35 U.S.C. 154(b) by 0 days.

(21) Appl. No.: 17/586,630

(22) Filed: Jan. 27, 2022

(65) Prior Publication Data

US 2022/0241252 A1 Aug. 4, 2022

Related U.S. Application Data

(60) Provisional application No. 63/143,750, filed on Jan. 29, 2021.

(51) Int. Cl.
A61K 31/437 (2006.01)
A61K 31/56 (2006.01)
A61P 11/00 (2006.01)

(52) U.S. Cl.
CPC ............ A61K 31/437 (2013.01); A61K 31/56 (2013.01); A61P 11/00 (2018.01)

(58) Field of Classification Search
CPC .............................. A61K 31/437; A61P 11/00
USPC ...................................................... 514/300
See application file for complete search history.

(56) References Cited

U.S. PATENT DOCUMENTS

| | | | |
|---|---|---|---|
| 6,395,747 | B1 | 5/2002 | Sakoda et al. |
| 7,709,495 | B2 * | 5/2010 | Jost-Price ............... A61P 11/00 514/180 |
| 8,138,201 | B2 | 3/2012 | Kalafer et al. |
| 9,314,452 | B2 | 4/2016 | Kalafer et al. |
| 2006/0160843 | A1 | 7/2006 | Johnson et al. |

FOREIGN PATENT DOCUMENTS

EP 0 320 002 A1 6/1989

OTHER PUBLICATIONS

Ohashi, M. et al.: Antagonist effect of KC-404, a new anti-asthmatic agent, on leukotriene-induced contractile responses in isolated guinea pig smooth muscle. Prostaglandins, vol. 32, pp. 875-888, 1986.*
Yuksel, H. et al.: Protective effect of leukotriene receptor antagonist Montelukast on smoking-induced lung injury in Wistar rats. Acta medica Okayama, vol. 57, pp. 13-19, 2003.*
Ohashi, M. et al.: Effect of Ibudilast, a novel antiasthmatic agent, on anaphylactic bronchoconstriction: predominant involvement of endogenous slow reacting substance of anaphylaxis. Int. Arch. Allergy Immunol., vol. 101, pp. 288-296, 1993.*
International Search Report and Written Opinion issued in International Patent Application No. PCT/US2022/013973, dated Apr. 19, 2022.
Wang, et al., "Inhaled Budesonide in Experimental Chlorine Gas Lung Injury: Influence of Time Interval between Injury and Treatment," Intensive Care Med., vol. 28, pp. 352-357 (2002).
Hedges, et al., "Acute Chlorine Gas Exposure," JACEP, vol. 8, No. 2, pp. 59-63 (Feb. 1979).
Joelsson, et al., "Azithromycin Ameliorates Sulfur Dioxide-induced Airway Epithelial Damage and Inflammatory Responses," Respiratory Research, vol. 21, No. 233, 11 pages (2020).
White, et al., ":Chlorine Gas Inhalation: Human Clinical Evidence of Toxicity and Experience in Animal Models," Proceedings of the American Thoracic Society, vol. 7, pp. 257-263 (2010).
Hoyle, "Mitigation of Chlorine Lung Injury by Increasing Cyclic AMP Levels," Proceedings of the American Thoracic Society, vol. 7, pp. 284-289 (2010).
Chang, et al., "Inhibition of Chlorine-Induced Lung Injury by the Type 4 Phosphodiesterase Inhibitor Rolipram," Toxicol. Appl. Pharmacol., vol. 263, No. 2, pp. 251-258 (Sep. 2012).
Malaviya, et al., "Inflammatory Mechanisms of Pulmonary Injury Induced by Mustards," Toxicol. Lett., vol. 244, 13 pages (Feb. 2016).
Cho, et al., "Allosteric Inhibition of Macrophage Migration Inhibitory Factor Revealed by Ibudilast," PNAS, vol. 107, No. 25, pp. 11313-11318 (2010).
Gibson et al., "The Inhibitory Profile of Ibudilast Against the Human Phosphodiesterase Enzyme Family," European Journal of Pharmacology, vol. 538, pp. 39-42 (2006).
Sanftner et al., "Cross-species comparisons of the pharmacokinetics of ibudilast," Xenobiotica, vol. 39, No. 12, pp. 964-977 (Nov. 2009). [Abstract].
Obernolte, R., et al. (1993) "The cDNA of a human lymphocyte cyclic-AMP phosphodiesterase (PDE IV) reveals a multigene family" Gene 129: 239-247.
Rile et al., "Potentiation of Ibudilast Inhibition of Platelet Aggregation in the Presence of Endothelial Cells," Thrombosis Research, 102 239-246 (2001).
Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).
Suzumura et al., "Ibudilast suppresses TNF.alpha. production by glial cells functioning mainly as type III phosphodiesterase inhibitor in NCS," Brain Research, 837:203-212 (1999).
Takuma et al., "Ibudilast attenuates actrocyte apoptsis via cyclic GMP signaling pathway in an in vitro reperfusion model," British Journal of Pharmacology, 133:841-848 (2001).
Jeffery et al., "The preparation and characterization of poly(lactide-co-glycolide) microparticles. II. The Entrapment of a Model Protein Using a (water-in-oil)-in-water Emulsion Solvent Evaporation Technique," Pharm. Research, vol. 10, pp. 362-368 (1993).
Yang, et al., "The Emerging Role of Toll-Like Receptor 4 in Myocardial Inflammation," Cell Death and Disease, vol. 7, e2234, 10 pages (2016).

* cited by examiner

Primary Examiner — Charanjit Aulakh
(74) Attorney, Agent, or Firm — FOLEY & LARDNER LLP

(57) ABSTRACT

A method of treating chemical-induced lung injury in a subject in need thereof includes administering to the subject a therapeutically effective amount of ibudilast, or a pharmaceutical salt thereof.

18 Claims, 1 Drawing Sheet

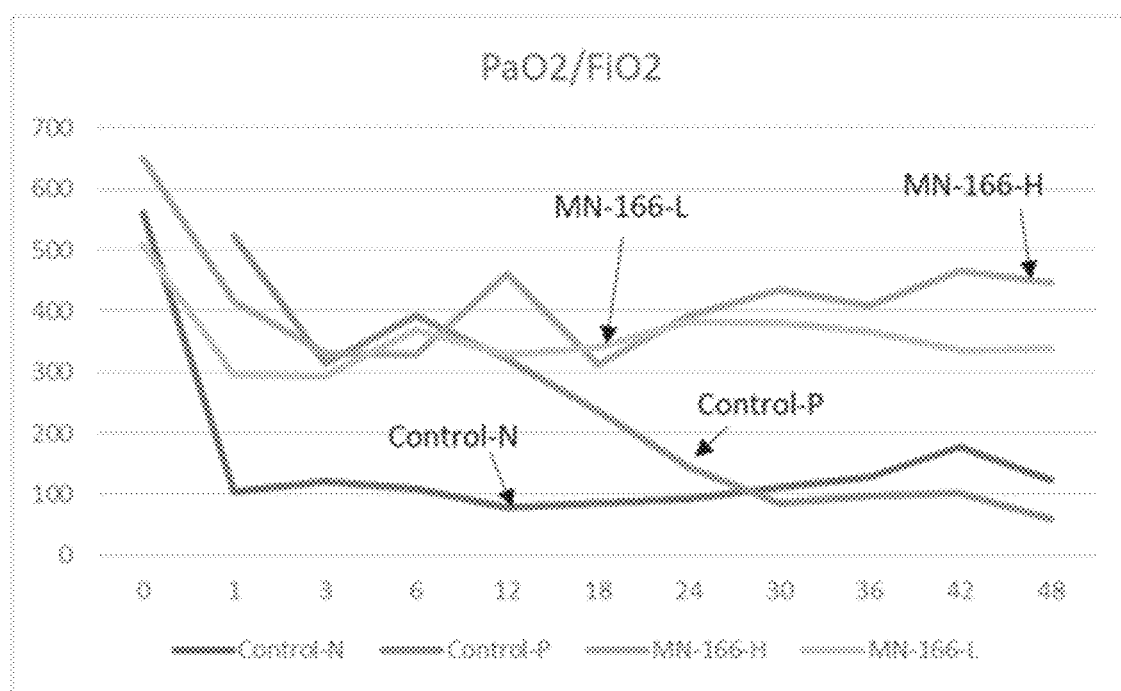

METHODS OF TREATING CHEMICAL GAS EXPOSURE

CROSS-REFERENCE TO RELATED APPLICATIONS

This application claims the benefit of U.S. Provisional Patent Application No. 63/143,750, filed on Jan. 29, 2021, which is incorporated by reference herein in its entirety.

BACKGROUND

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News.Medical.Net; Pharmaceutical News, 2 Aug. 2005). As disclosed in this publication, this clinical trial was expected to treat "relapsing-remitting MS," however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. U.S. Patent Application Publication No. 20060160843 discloses ibudilast for the treatment of intermittent and short term pain, however, this is not pain related to a progressive neurodegenerative disease. However, U.S. Pat. No. 9,314,452 discloses ibudilast as a treatment for amyotrophic lateral sclerosis, a progressive neurodegenerative disease. Similarly, U.S. Pat. No. 8,138,201 discloses ibudilast as a treatment for primary progressive multiple sclerosis and/or secondary progressive multiple sclerosis.

While the use of ibudilast for a number of varying indications has been reported to date, to the best of the inventors' knowledge, its use in treating chemical-induced acute lung injury in patients has heretofore remained largely unexplored.

SUMMARY

In one aspect, disclosed herein is a method of treating chemical-induced lung injury in a subject in need thereof, the method comprising, consisting essentially of, or consisting of administering to the subject a therapeutically effective amount of ibudilast, or a pharmaceutical salt thereof.

In some embodiments, the lung injury is induced by a chemical selected from chlorine, sulfur mustard gas, phosgene, Lewisite, hydrogen chloride, sulfur dioxide, hydrogen sulfide, nitrogen dioxide, ammonia, hydrofluoric acid, ozone, methyl isocyanate, and a combination of two or more thereof.

In some embodiments, the lung injury comprises chemical burns, pulmonary edema, laryngeal edema, lung tissue apoptosis, pneumonia, pneumonitis, bronchitis, bronchiolitis, fibrosis, acute respiratory distress syndrome, respiratory tract spasm, or a combination of two or more thereof.

In some embodiments, ibudilast, or the pharmaceutically acceptable salt thereof, is administered orally. In some embodiments, ibudilast, or the pharmaceutically acceptable salt thereof, is administered intravenously. In some embodiments, ibudilast, or the pharmaceutically acceptable salt thereof, is administered by subcutaneous injection. In some embodiments, ibudilast, or the pharmaceutically acceptable salt thereof, is administered by intramuscular injection. In some embodiments, ibudilast, or the pharmaceutically acceptable salt thereof, is administered by inhalation.

In some embodiments, ibudilast, or the pharmaceutically acceptable salt thereof, is administered for 1, 2, 3, 4, 5, 6, 7, 8, 9, or 10 days, or more. In some embodiments, ibudilast, or the pharmaceutically acceptable salt thereof, is administered for at least 3 months.

In some embodiments, ibudilast, or the pharmaceutically acceptable salt thereof, is administered at least once daily. In some embodiments, ibudilast, or the pharmaceutically acceptable salt thereof, is administered twice daily.

In some embodiments, the therapeutically effective amount of ibudilast, or the pharmaceutically acceptable salt thereof, is from 0.1 mg to 720 mg per day. In some embodiments, the therapeutically effective amount of ibudilast, or the pharmaceutically acceptable salt thereof, is from 30 mg to 200 mg per day. In some embodiments, the therapeutically effective amount of ibudilast, or the pharmaceutically acceptable salt thereof, is 40 mg to 600 mg daily. In some embodiments, the therapeutically effective amount of ibudilast, or the pharmaceutically acceptable salt thereof, is 100 mg to 480 mg daily. In some embodiments, the therapeutically effective amount of ibudilast, or the pharmaceutically acceptable salt thereof, is selected from the group consisting of 30 mg/day, 60 mg/day, 90 mg/day, 100 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

In some embodiments, the therapeutically effective amount is administered as a single dose or is divided into two, three, or four doses. In some embodiments, ibudilast is administered continually.

In some embodiments, ibudilast, or the pharmaceutically acceptable salt thereof, is the only active agent administered to the patient. In some embodiments, ibudilast, or the pharmaceutically acceptable salt thereof, is administered to the patient with at least one other active agent. In some embodiments, the at least one other active agent comprises or consists of a corticosteroid.

BRIEF DESCRIPTION OF THE DRAWING

The FIGURE depicts $PaO_2/FiO_2$ results for 4 animals (negative control (control-N); positive control (control-P); High MN-166 dose; Low MN-166 dose) tested in an acute lung injury sheep model.

DETAILED DESCRIPTION

The practice of the present disclosure will employ, unless otherwise indicated, conventional methods of chemistry, biochemistry, and pharmacology, within the skill of the art. Such techniques are explained fully in the literature. See, e.g.; A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

Before describing the present disclosure in detail, it is to be understood that this disclosure is not limited to particular administration modes, patient populations, and the like, as such may vary, as will be apparent from the accompanying description.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present disclosure, the following terminology will be used in accordance with the definitions described below.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention. When an embodiment is defined by one of these terms (e.g., "comprising") it should be understood that this disclosure also includes alternative embodiments, such as "consisting essentially of" and "consisting of" for said embodiment.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutraceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent may include ibudilast or a pharmaceutically acceptable salt thereof.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

The terms "subject," "individual" or "patient" are used interchangeably herein and refer to a vertebrate, preferably a mammal. Mammals include, but are not limited to, mice, rodents, rats, simians, humans, farm animals, dogs, cats, sport animals and pets.

The terms "pharmacologically effective amount" or "therapeutically effective amount" of a composition or agent, as provided herein, refer to a nontoxic but sufficient amount of the composition or agent to provide the desired response, such as a reduction or recovery from chemical-induced lung injury. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about," will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

As used herein, the term "treatment" or "treating" means any treatment of a condition or associated disorder, in a patient, including inhibiting the condition or associated disorder, that is, arresting or suppressing the development of clinical symptoms, such as chemical burns, pulmonary edema, laryngeal edema, lung tissue apoptosis, pneumonia, pneumonitis, bronchitis, bronchiolitis, fibrosis, acute respiratory distress syndrome, respiratory tract spasm, or a combination of two or more thereof, and/or relieving the condition or associated disorder that is causing the regression of clinical symptoms.

In some aspects, the term treating refers to an improvement in clinical outcomes due to delayed administration of ibudilast after lung injury and development of symptoms. The term "clinical outcome" refers to any clinical observation or measurement relating to a patient's reaction to a therapy. Non-limiting examples of clinical outcomes include clinical observation of or measurement of alveolar inflammation, pulmonary edema, lung tissue apoptosis, lung tissue necrosis, airway destruction, or any combination thereof, in the patient in reaction to the therapy.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

The methods of the disclosure are based upon administration of the molecule, ibudilast. Ibudilast is a small molecule drug (molecular weight of 230.3) having the structure shown below.

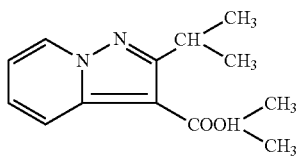

Ibudilast is also found under ChemBank ID 3227, CAS #50847-11-5, and Beilstein Handbook Reference No. 5-24-03-00396. Its molecular formula corresponds to C14H18N2O. Ibudilast is also known by various chemical names including 2-methyl-1-(2-(1-methylethyl)pyrazolo(1,5-a)pyridin-3-yl)1-propanone; 3-isobutyryl-2-isopropylpyrazolo(1,5-a)pyridine; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is Ketas®. Ibudilast, as referred to herein, is meant to include any and all pharmaceutically acceptable salt forms thereof, prodrug forms (e.g., the corresponding ketal, oxime, oxime derivative, hydrazone, or semicarbazone), solvates, and the like, as appropriate for use in its intended formulation for administration.

Ibudilast is also a selective inhibitor of cyclic nucleotide phosphodiesterases (PDEs) 3A, 4, 10A1 and 11A1 (Gibson et al., Eur J Pharmacol 538: 39-42, 2006), has toll-like receptor-4 (TLR4) antagonistic activity (Yang et al., Cell Death and Disease (2016) 7, e2234; doi:10.1038/cddis.2016.140) and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: $Ca^{2+}$/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting in the suppression of both pro-inflammatory mediator and neuroactive mediator release. Ibudilast may also suppress the production of pro-inflammatory cytokines (IL-1ß, TNF-α) and may enhance the production of the anti-inflammatory cytokines (IL-4, IL-10). References related to the foregoing include the following: Obernolte, R., et al. (1993) "The cDNA of a human lymphocyte cyclic-AMP phosphodiesterase (PDE IV) reveals a multigene family" Gene 129: 239-247; Rile, G., et al. (2001) "Potentiation of ibudilast inhibition of platelet aggregation in the presence of endothelial cells" Thromb. Res. 102: 239-246; Souness, J. E., et al. (1994) "Possible role of cyclic AMP phosphodiesterases in the actions of ibudilast on eosinophil thromboxane generation and airways smooth muscle tone" Br. J. Pharmacol. 111: 1081-1088; Suzumura, A., et al. (1999) "Ibudilast suppresses TNF.alpha. production by glial cells functioning mainly as type III phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" Br. J. Pharmacol. 133: 841-848. With regards to the treatment of cancers of the CNS, ibudilast exhibits good CNS penetration. (Sanftner et al Xenobiotica 2009 39: 964-977).

Ibudilast is also an allosteric inhibitor of p-hydoxyphenylpyruvate (HPP) tautomerase activity of macrophage inhibitory factor (MIF) (Cho et al., PNAS-USA, 2010 June 107: 11313-8), thereby inhibiting the catalytic and chemotactic functions of MIF. It was unexpectedly found by the inventors that ibudilast also lowers plasma level of MIF. Such a decrease in MIF plasma level is unexpected since there is no known connection between allosteric inhibition of MIF and MIF concentration in plasma. However, since MIF is involved in intracellular signaling through activation of CD74 in a complex with CD44 or the chemokine receptors CXCR2 and CXCR4, both the MIF inhibition and decrease in MIF plasma level by ibudilast can minimize the proinflammatory action of MIF.

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Methods of Treatment and Administration

As set forth above, in one aspect, the present disclosure is directed to a methods of treating chemical-induced lung injury in a subject in need thereof, the method comprising, consisting essentially of, or consisting of administering to the subject a therapeutically effective amount of ibudilast, or a pharmaceutical salt thereof. Such administration is effective to attenuate or reverse chemical-induced lung injury in the subject. The lung injury comprises or consists of chemical burns, pulmonary edema, laryngeal edema, lung tissue apoptosis, pneumonia, pneumonitis, bronchitis, bronchiolitis, fibrosis, acute respiratory distress syndrome, respiratory tract spasm, or a combination of two or more thereof.

In some embodiments, ibudilast or a pharmaceutically acceptable salt thereof is administered at a daily dosage amount ranging from about 0.1 mg to 720 mg daily, from about 30 mg to 200 mg daily, from about 40 mg to 600 mg daily, or from about 100 mg to 480 mg daily. In some embodiments, a reduction of the plasma level of macrophage migratory inhibitory factor in the subject is observed within 12 hours after a first dose of ibudilast is administered. In some embodiments, a reduction of the plasma level of macrophage migratory inhibitory factor in the subject is observed within 12 hours after administration of ibudilast for 1, 2, 3, 4, 5, 6, 7, 8, 9, or 10 days.

Ibudilast administration may be accomplished through various modes of delivery of ibudilast comprising formulations. Preferred methods of delivery of ibudilast-based therapeutic formulations include systemic and localized delivery. Such routes of administration include but are not limited to, oral, intra-arterial, intrathecal, intraspinal, intramuscular, intraperitoneal, intranasal, and inhalation routes.

More particularly, an ibudilast-based formulation of the present disclosure may be administered for therapy by any suitable route, including without limitation, oral, rectal, nasal, topical (including transdermal, aerosol, buccal and sublingual), vaginal, parenteral (including subcutaneous, intravenous, intramuscular, and intradermal), intrathecal, and pulmonary. In some embodiments, the ibudilast-based formulation is administered orally. In some embodiments, the ibudilast-based formulation is administered through an injection. The preferred route will, of course, vary with the condition and age of the recipient, the particular syndrome being treated, and the specific combination of drugs employed.

In some embodiments, the ibudilast or pharmaceutically acceptable salt thereof is administered orally. In some embodiments, the ibudilast or pharmaceutically acceptable salt thereof is administered through an injection.

An ibudilast composition of the present disclosure, when comprising more than one active agent, may be administered as a single combination composition comprising a combination of ibudilast and at least one additional active agent. In terms of patient compliance and ease of administration, such an approach is preferred, since patients are often averse to taking multiple pills or dosage forms, often multiple times daily, over the duration of treatment. Alternatively, the combination of the disclosure is administered as separate dosage forms. In instances in which the drugs comprising the therapeutic composition of the disclosure are administered as separate dosage forms and co-administration is required, ibudilast and each of the additional active agents may be administered simultaneously, sequentially in any order, or separately.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount of ibudilast or pharmaceutically acceptable salt thereof will range from a total daily dosage of about 0.1 mg/day to 720 mg/day, about 40-600 mg/day, or about 100-480 mg/day, or more preferably, in an amount between about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, the therapeutically effective amount of ibudilast or pharmaceutically acceptable salt thereof is from about 30-200 mg/day, administered as either a single dosage or as multiple dosages. In some embodiments, multiple dosages include two, three, or four doses per day.

Preferred dosage amounts include dosages greater than about 20 mg BID or TID. That is to say, a preferred dosage amount is greater than about 30 mg/day, 60 mg/day, 90 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day or more.

In some embodiments, the therapeutically effective amount of ibudilast or pharmaceutically acceptable salt thereof is at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, or at least 720 mg/day. In some embodiments, the therapeutically effective amount of ibudilast or pharmaceutically acceptable salt thereof is at least 60 mg/day. In some embodiments, the therapeutically effective amount of ibudilast or pharmaceutically acceptable salt thereof is at least 100 mg/day.

Depending upon the dosage amount and precise condition to be treated, administration can be one, two, three, or four times daily for a time course of one day to several days, weeks, months, and even years, and may even be for the life of the patient. Illustrative dosing regimens will last a period of at least about a week, from about 1-4 weeks, from 1-3 months, from 1-6 months, from 1-52 weeks, from 1-24 months, or longer. In some embodiments, the ibudilast or the pharmaceutically acceptable salt thereof is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In some embodiments, the ibudilast or the pharmaceutically acceptable salt thereof is administered for three months or less. In some embodiments, the ibudilast or the pharmaceutically acceptable salt thereof is administered for at least three months. In some embodiments, the ibudilast or the pharmaceutically acceptable salt thereof is administered for at least six months.

In some embodiments, the ibudilast or the pharmaceutically acceptable salt thereof is administered for 1, 2, 3, 4, 5, 6, 7, 8, 9, 10, 11, or 12 months, or more. In some embodiments, the ibudilast or the pharmaceutically acceptable salt thereof is administered for about 1, 2, 3, 4, 5, 6, 7, 8, 9, or 10 years, or more. In some embodiments, the ibudilast or the pharmaceutically acceptable salt thereof is administered for at least 1 year. In some embodiments, the ibudilast or the pharmaceutically acceptable salt thereof is administered for at least 2 years. In some embodiments, the ibudilast or the pharmaceutically acceptable salt thereof is administered as a one-time single dose.

In some embodiments, the therapeutically effective amount of ibudilast or the pharmaceutically acceptable salt thereof is administered in a single dosage per day. In some embodiments, the therapeutically effective amount of ibudilast or the pharmaceutically acceptable salt thereof is administered in two dosages per day. In some embodiments, the therapeutically effective amount of ibudilast or the pharmaceutically acceptable salt thereof is administered in three dosages per day. In some embodiments, the therapeutically effective amount of ibudilast or the pharmaceutically acceptable salt thereof is administered in four dosages per day. In some embodiments, the therapeutically effective amount of ibudilast or the pharmaceutically acceptable salt thereof is administered continually.

In some embodiments, the ibudilast or pharmaceutically acceptable salt thereof is administered at least once daily. In some embodiments, the ibudilast or pharmaceutically acceptable salt thereof is administered at least twice daily. In some embodiments, the ibudilast or pharmaceutically acceptable salt thereof is administered once daily. In some embodiments, the ibudilast or pharmaceutically acceptable salt thereof is administered twice daily.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Formulations

Ibudilast may be administered in a composition of formulation which may optionally contain one or more additional components as described below.

Excipients/Carriers

In addition to ibudilast or a pharmaceutically acceptable salt thereof, the compositions of the disclosure may further comprise one or more pharmaceutically acceptable excipients or carriers. Exemplary excipients include, without limitation, polyethylene glycol (PEG), PEG 400, (2-Hydroxypropyl)-β-cyclodextrin, hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the disclosure may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like, and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations. In some embodiments, the surfactant may comprise polyethoxylated castor oil derivatives (e.g., Cremophor EL, Kolliphor ELP, and the like). Other non-limiting excipients include alcohol (e.g., ethanol), propylene glycol, glyderol, or polyethyleneglycol (PEG).

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99/o by weight, preferably from about 5% to about 98% by weight, more preferably from about 15% to about 95% by weight of the excipient. In general, the amount of excipient present in an ibudilast composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", 19th ed., Williams & Williams, (1995), the "Physician's Desk Reference", 52.sup.nd ed., Medical Economics, Montvale, N.J. (1998), and Kibbe, A. H., Handbook of Pharmaceutical Excipients, 3.sup.rd Edition, American Pharmaceutical Association, Washington, D.C., 2000.

Other Actives

A formulation (or kit) in accordance with the disclosure may contain, in addition to ibudilast or a pharmaceutically acceptable salt thereof, one or more other therapeutic active agents.

Preferably, the one or more other therapeutic agent is one that possesses a mechanism of action different from that of ibudilast. Such active ingredients can be found listed in the FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

In some embodiments, the one or more other therapeutic active agents are one or more corticosteroids. Non-limiting examples of corticosteroids include cortisone, prednisone, prednisolone, methylprednisolone, dexamethasone, betamethasone, hydrocortisone, amcinonide, budesonide, desonide, fluocinolone acetonide, fluocinonide, halcinonide, triamcinolone acetonide, beclometasone, fluocortolone, halometasone, mometasone, alclometasone dipropionate, betamethasone dipropionate, betamethasone valerate, clobetasol propionate, clobetasone butyrate, fluprednidene acetate, and mometasone furoate.

The dosage amounts provided above are meant to be merely guidelines, the precise amount of a secondary active agent to be administered during combination therapy with ibudilast or the pharmaceutically acceptable salt thereof will, of course, be adjusted accordingly and will depend upon factors such as intended patient population, the particular symptom or condition to be treated, potential synergies between the active agents administered, and the like, and will readily be determined by one skilled in the art based upon the guidance provided herein.

Sustained Delivery Formulations

Preferably, the compositions are formulated in order to improve stability and extend the half-life of ibudilast or the pharmaceutically acceptable salt thereof. For example, ibudilast or the pharmaceutically acceptable salt thereof may be delivered in a controlled or extended-release formulation. Controlled or extended-release formulations are prepared by incorporating ibudilast or the pharmaceutically acceptable salt thereof into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast or the pharmaceutically acceptable salt thereof can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; and McGee et al., J. Microencap. (1996).

Extended release polymers suitable for this purpose are known in the art and include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleic anhydride copolymers and the like; ethylacrylate-methylmethacrylate copolymers; aminoalkyl methacrylate copolymers; and mixtures thereof.

Delivery Forms

The ibudilast or pharmaceutically acceptable salt thereof compositions described herein encompass all types of formulations, and in particular, those that are suited for systemic or intrathecal administration. Oral dosage forms include tablets, lozenges, capsules, syrups, oral suspensions, emulsions, granules, and pellets. In some embodiments, the oral dosage form is a tablet. In some embodiments, the tablet is an extended release tablet. In some embodiments, the oral dosage form is a capsule. In some embodiments, the capsule is an extended release capsule.

Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, an ibudilast or pharmaceutically acceptable salt thereof composition of the disclosure is one suited for oral administration.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx® (Aradigm), the Ultravent® (Mallinkrodt), and the Acorn II® (Marquest Medical Products). A composition of the disclosure may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the disclosure are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the disclosure may also be an extended release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the disclosure may optionally include other agents conventional in the pharmaceutical arts and particular type of formulation being employed, for example, for oral administration forms, the composition for oral administration may also include additional agents as sweeteners, thickeners or flavoring agents.

Kits

Also provided herein is a kit containing at least one composition of the disclosure, accompanied by instructions for use.

In some embodiments, the kit contains at least one combination composition described herein, accompanied by instructions for use. For example, in instances in which each of the drugs themselves are administered as individual or separate dosage forms, the kit comprises ibudilast in addition to each of the drugs making up the composition of the disclosure, along with instructions for use. The drug components may be packaged in any manner suitable for administration, so long as the packaging, when considered along with the instructions for administration, clearly indicates the manner in which each of the drug components is to be administered.

For example, for an illustrative kit comprising ibudilast and one other active agent, the kit may be organized by any appropriate time period, such as by day. As an example, for Day 1, a representative kit may comprise unit dosages of each of ibudilast and the one other active agent. If each of the drugs is to be administered twice daily, then the kit may contain, corresponding to Day 1, two rows of unit dosage forms of each of ibudilast and the one other active agent, along with instructions for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister packs, desiccants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1: Chlorine Efficacy Study in Mice

The purpose of this study is to evaluate the efficacy of ibudilast against whole body chlorine inhalation exposure in C57BL/6 mice. Animals are exposed to chlorine gas for 11 minutes at 575 ppm ($LD_{50/7 \ d}$). Groups receive ibudilast once daily starting at 1 hr post chlorine exposure (low dose: about 4-6 mg/kg; medium dose: about 6-7.5 mg/kg; high dose: about 7.5-10 mg/kg) according to the table below by tail vein injection and continued daily for 7 days. A group is exposed to a PDE4 inhibitor (rolipram) and serves as a positive control. At 24 hr post chlorine exposure, animals undergo pulmonary function testing using an EMKA whole body pulmonary function system, followed by collection of lavage fluid for analysis of cell counts and differentials, and collection of the left lung lobe for histopathology analysis. Prior to conduct of the efficacy evaluation, a group of 10 animals (Group 0 in the table below) are exposed to chlorine to verify the lethality of the 575 ppm, 11 min exposure. At the conclusion of this portion of the study, animals are euthanized with no terminal procedures conducted.

Study Design:

| Group | Treatment | Dose Time (h) | Challenge | Male | Nx Timepoint (d) |
|---|---|---|---|---|---|
| Group 0 | NA | NA | chlorine | 10 | 3 (euthanasia only) |
| Group 1 | Vehicle | 1 | chlorine | 20 | 8 |
| Group 2 | ibudilast (low) | 1 | chlorine | 20 | 8 |
| Group 3 | ibudilast (medium) | 1 | chlorine | 20 | 8 |
| Group 4 | ibudilast (high) | 1 | chlorine | 20 | 8 |
| Group 5 | PDE4 inhibitor | 1 | chlorine | 20 | 8 |
| Group 6 | NA | NA | air | 20 | 8 |

A total of 139 C57BL/6 mice (including spares) are purchased. Animals are approximately 8-10 weeks in age upon arrival and undergo a minimum of a 7 day quarantine.

After administration of chlorine, animals are monitored continuously for the first 4 hr. During this time, the animals remain in the exposure facility with external noises (i.e. slamming of doors) kept to a minimum. Animals are monitored a minimum of 3 additional times (~5-7 hr post-chlorine, ~11-13 hr post-chlorine, and ~17-19 hr post-chlorine). After 24 hr, animals are monitored once daily through the duration of the study. Animals are monitored for lethargy, hunched posture, respiratory distress, and excessive urination and diarrhea. Body weights are collected prior to chlorine exposure and at necropsy.

At scheduled euthanasia (Day 8) post-chlorine exposure animals undergo pulmonary function testing. Only animals surviving to scheduled euthanasia undergo pulmonary function analysis. Animals determined to be moribund do not undergo pulmonary function testing.

At the conclusion of the study, 8 days post chlorine exposure, animals are euthanized. Moribund animals are euthanized as needed throughout the duration of the study. Necropsy is conducted on Day 8 following chlorine exposure. The left lobes are fixed for histopathology. The right lobes are lavaged and flash frozen. Collected lavage samples are analyzed for cell counts and differentials.

Example 2: Chlorine-Induced Acute Lung Injury (ALI) Sheep Model: Protocol 1

The ovine model allows measurement of various sophisticated cardiopulmonary variables that can be used as endpoints for treatment or fluid resuscitation. Unlike rodents, sheep can be intubated or tracheostomized with minimum damage to the airway and can be mechanically ventilated using standard clinical equipment. Additionally, ovine models closely mimic clinical situations in terms of basic standard care of acute lung injury, i.e., fluid resuscitation, monitoring of pulmonary function, and mechanical ventilation. Their blood volume is large enough to supply samples for frequent intermittent blood gas analysis and circulating cells counts without aggravating hypovolemic shock. They can be easily studied in the un-anesthetized state. Importantly, sheep responses (both physiologic and genomic) to inflammation are similar in nature to those in humans unlike porcine and rodent models.

Surgical preparation: After at least 7 to 14 days quarantine time, sheep are surgically prepared for measurement of heart rate, systemic arterial pressure, pulmonary arterial pressure (including cardiac output), pulmonary arterial wedge pressure, left atrial pressure, core body temperature, and central venous pressure. These instrumental procedures are performed under isoflurane anesthesia via endotracheal tube.

Briefly, 36 female adult sheep are pre-anesthetized with 15 to 20 mg/kg intramuscular ketamine followed by 10 to 15 mg/kg IV ketamine. After endotracheal intubation, the anesthesia is maintained using inhaled isoflurane. The sheep are mechanically ventilated, and surgery is conducted utilizing strict aseptic technique. Analgesia is provided by long acting (72 h) buprenorphine.

Sixteen-gauge, 24 inch arterial and venous catheters are placed in the descending aorta and vena cava using a cut down over the femoral artery and vein. Catheters are sutured in place using 1/0 Ethibond suture, exteriorized through a small incision in the flank skin, and the wound are closed in a simple continuous pattern with 2/0 Vicryl. A Swan-Ganz thermal dilution pulmonary arterial catheter are positioned in the pulmonary artery via the right external jugular vein using a commercially available percutaneous catheter introducer system. A catheter (0.062 inch internal diameter, 0.125 inch outer diameter) is also positioned in the left atrium through the fifth intercostal space. To prevent possible arrhythmia during the cannulation of the left atrium of the heart, 1 to 3 mg/kg of lidocaine is topically applied to the surface of heart. The tubing is exteriorized through a small stab incision in the chest wall. The ribs are opposed with 2 simple interrupted 1/0 or 2/0 stainless steel wire sutures. The muscles and subcutaneous tissues are sutured with 2/0 Vicryl in 2 layers using a simple continuous pattern. The skin is closed with 2/0 Vicryl in a simple continuous pattern. During the surgical procedure, to reduce the risk of infection, an IV double dose of cefazolin (2 g) is administered. Then, sheep are allowed to recover from anesthesia and are given 5 to 7 days to heal from the surgical procedure with free access to food and water before they undergo the ALI protocol. Surgical and post-surgical analgesia are provided with subcutaneous injection of long-acting (72 hr) buprenorphine$^{SR}$ (0.1 to 0.27 mg/kg).

During the recovery period, sheep are connected to hemodynamic monitors, IV fluid resuscitated with lactated Ringer's solution, and provided with food and water. The vascular catheters and lines are continuously flushed with heparinized saline.

Baseline Variables: After 5 to 7 days of surgical recovery, baseline measurements of respiratory and hemodynamic variables are taken in awake, un-anesthetized sheep.

Baseline variables include the following:

Cardiopulmonary Hemodynamics:
 Heart rate;
 Mean arterial pressure;
 Cardiac output;
 Left atrial pressure;
 Central venous pressure;
 Pulmonary arterial pressure;
 Pulmonary artery occlusion pressure; and
 Calculated variables: cardiac index, systemic vascular and pulmonary arterial resistance index, pulmonary capillary pressure, and left and right ventricular stroke volume index.
 Core body temperature Arterial and Venous Blood Gas Analysis, Complete Blood Cell Count:
- $PO_2$, $CO_2$, $SO_2$, hematocrit, hemoglobin, pH, electrolytes (Na, K, Ca, Cl), lactate, and glucose;
- Calculated variables—partial pressure of oxygen in arterial blood ($PaO_2$)/partial pressure of inspired oxygen ($FiO_2$) ratio and pulmonary shunt fraction
- Complete blood cell count.

Exclusion criteria: If any of following symptoms is present, sheep are removed from the study:
- $PaO_2$<90 mmHg at room air,
- Hematocrit <20%,
- Hemoglobin <7 g/dL,
- Core body temperature >40° C. (normal sheep body temperature is approximately 39.6° C.),
- White cells >10 k/μL.

Induction of ALI: Immediately prior to study initiation, sheep are subjected to ketamine anesthesia at 5 mg/kg, via IV injection, followed by a long-acting (72 h) buprenorphine analgesia at 0.1 mg/kg, via SC injection. A tracheostomy is performed, and anesthesia maintained using IV Propofol with initial bolus of 50 mg thereafter titrated to effect. Sheep are ventilated at a positive end-expiratory pressure (PEEP) of 5 cm $H_2O$, with a tidal volume (TV) 12 mL/kg. A Foley catheter is passed through the urethra to catheterize the bladder to allow for continuous urine collection for measurement of urine output. Animals are to receive a chest X-ray prior to chlorine exposure and prior to euthanasia (if applicable).

Injury is induced by endotracheal delivery of chlorine, at concentration of 150 or 200 ppm in air, for 30 min via a closed ventilatory circuit connected to the chlorine tank. The ventilator is set at 12 mL/kg of tidal volume, 5 cm $H_2O$ of PEEP, and 20 b/min of respiratory rate. The setting enables comparable exposure among the animals.

The chlorine level of inhaled gas is certified as a premixed blend of chlorine and medical grade air supplied via the ventilator without dilution. The total flow of chlorine/air mixture is determined via a mass flow meter with stainless steel components placed immediately after the regulator. The chlorine tank is preheated (24 h) with electric warmer to 40° C. to properly mix the gas. During the 30-min injury period, blood gas analysis is performed every 10 minutes and cardiopulmonary variables are recorded. During the exposure, a possible chlorine leak is monitored at least by 2 monitors. The exposure is performed in a special room with negative pressure and toxic gas evacuation hood. At least 3 TICU personnel wearing designated PPE including respirator induce the exposure and provide care. After the 30-minute chlorine exposure, the sheep are ventilated with air (no chlorine) 10 minutes to flush out the chlorine residue from both sheep airways and the ventilatory circuits. Then, sheep are disconnected from the ventilator and transferred to the ICU station.

Post-injury monitoring: After the transferring the sheep to the ICU station, sheep are placed on a mechanical ventilator (Avea APVcmv mode: RR 20 b/m, TV 12 mL/kg, PEEP 5 cm H2O), connected to the hemodynamic monitors and monitored for 48 hrs in a conscious state. Sheep are humanely euthanized at 48 hrs after the injury under deep anesthesia and analgesia. If during the study, one of following occurs, and not reversed for 1 h despite resuscitation, sheep are humanely euthanized.
- $PaO_2/FiO_2$ ratio <50 mmHg
- $PaCO_2$>90 mmHg
- MAP <50 mmHg.

Grouping and treatment: After the injury, sheep are randomly assigned to one of following 4 groups:
1. Control: exposed to chlorine, treated with equal amount of vehicle;
2. Positive Control: exposed to chlorine, treated with PDE4 inhibitor (rolipram).
3. MN-166 (high dose): exposed to chlorine, treated with MN-166 high dose (up to 100 mg/kg); and
4. MN-166 (low dose): exposed to chlorine, treated with MN-166 low dose (up to 50 mg/kg).

Each group includes 8 sheep. The total number of sheep for entire study is 36 including 1 sheep per group for possible technical errors (36=8 sheep per group×4 groups+4 sheep (1 sheep per group) for experimental failure/errors). During the study period, sheep are fluid resuscitated with lactated Ringer's solution 2 mL/kg/h.

Endpoints: Following treatment, study assessments are performed in the same manner as baseline variables. A description of each assessment is provided below.
1. Pulmonary function: is assessed by 1) intermittent (every 6 h) arterial and venous blood gas analyses, which include arterial and venous blood $PaO_2$, $CO_2$, $SO_2$, base excess, pH, and $SO_2$. Additionally, arterial hematocrit, hemoglobin, electrolytes, glucose, and lactate are measured every 6 h. $PaO_2/FiO_2$ ratio are calculated to determine severity of ARDS. Bilateral pulmonary infiltration is confirmed by chest X-ray taken at the end of study. The chest X-ray is taken before the injury as well. Pulmonary shunt fraction is calculated by a standard formula; and 2) pulmonary mechanics i.e., lung compliance, airway peak and pause pressures and dead space are taken every 6 h from ventilator readouts.
2. Lung injury and edema formation is assessed postmortem by histology (alveolar and interstitial edema), and lung water content (wet-to-dry weight ratio) in addition to chest X-ray. Lung tissue histology also include parenchymal congestion, hemorrhage, accumulation of inflammatory cells, atelectasis, and airway epithelia exfoliation.
3. Cardiopulmonary hemodynamics is continuously monitored, and variables indicated in baseline are recorded every 6 h.
4. Systemic vascular permeability is assessed by determination of accumulated net fluid balance for 48 h (fluid in and urinary output measured every 6 h), plasma protein, fluid accumulation in body cavities (thoracic and abdominal).
5. Complete peripheral blood cell count is determined every 6 h.

Sampling: 1) Arterial blood is taken every 6 h first 24 h and every 12 h at second 24 h, and aliquots of plasma and serum is stored at 20° C. for future assessments; 2) aliquots of urine are taken at indicated time points and stored in at 20° C.; 3) Bronchoalveolar lavage is performed at the end of study and aliquots are frozen and stored at 20° C.; and 4) animals are humanely euthanized at 48 h after the injury and aliquots of trachea, bronchi, lung parenchyma, heart, liver, and kidney stored frozen at −80° C. and fixed in formalin. The volume of thoracic and abdominal fluid is measured, if present, and total protein is measured.

Statistical analysis: Statistical analysis is performed using GraphPad Prism 8 software with two-or-one way ANOVA and T-test when applicable.

Pulmonary function. Respiratory parameters are assessed intermittently, and quantifiable comparisons made between treatment groups. The relative severity of ARDS in the various treatment groups is assessed from calculated $PaO_2$/$FiO_2$ ratios. Other variables to be assessed include pulmonary infiltration, pulmonary shunt fraction and pulmonary mechanics.

Lung injury and edema formation. Comparison of histological samples, post-mortem, are evaluated and comparisons made between treatment groups to assess efficacy of ibudilast drug treatment. The extent of hemorrhage, accumulation of inflammatory cells, atelectasis, and airway epithelia exfoliation is quantified. Differences in lung water content are determined by chest X-ray and compared.

Systemic vascular permeability. Accumulated net fluid balance is measured over a 48-hour period and comparison of drug-treated, untreated and positive control groups are compared to assess efficacy.

Example 3: Chlorine-Induced Acute Lung Injury (ALI) Sheep Model: Protocol 2

Surgical preparation: After at least 7 to 14 days quarantine time, sheep were surgically prepared for measurement of heart rate, systemic arterial pressure, pulmonary arterial pressure (including cardiac output), pulmonary arterial wedge pressure, left atrial pressure, core body temperature, and central venous pressure. These instrumental procedures were performed under isoflurane anesthesia via endotracheal tube.

Briefly, 36 female adult sheep were pre-anesthetized with 15 to 20 mg/kg intramuscular ketamine followed by 10 to 15 mg/kg IV ketamine. After endotracheal intubation, the anesthesia was maintained using inhaled isoflurane. The sheep were mechanically ventilated, and surgery was conducted utilizing strict aseptic technique. Analgesia was provided by long acting (72 h) buprenorphine.

Sixteen-gauge, 24 inch arterial and venous catheters were placed in the descending aorta and vena cava using a cut down over the femoral artery and vein. Catheters were sutured in place using 1/0 Ethibond suture, exteriorized through a small incision in the flank skin, and the wound was closed in a simple continuous pattern with 2/0 Vicryl. A Swan-Ganz thermal dilution pulmonary arterial catheter were positioned in the pulmonary artery via the right external jugular vein using a commercially available percutaneous catheter introducer system. A catheter (0.062 inch internal diameter, 0.125 inch outer diameter) was also positioned in the left atrium through the fifth intercostal space. To prevent possible arrhythmia during the cannulation of the left atrium of the heart, 1 to 3 mg/kg of lidocaine was topically applied to the surface of heart. The tubing was exteriorized through a small stab incision in the chest wall. The ribs were opposed with 2 simple interrupted 1/0 or 2/0 stainless steel wire sutures. The muscles and subcutaneous tissues were sutured with 2/0 Vicryl in 2 layers using a simple continuous pattern. The skin was closed with 2/0 Vicryl in a simple continuous pattern. During the surgical procedure, to reduce the risk of infection, an IV double dose of cefazolin (2 g) was administered. Then, sheep were allowed to recover from anesthesia and were given 5 to 7 days to heal from the surgical procedure with free access to food and water before they underwent the ALI protocol. Surgical and post-surgical analgesia were provided with subcutaneous injection of long-acting (72 hr) buprenorphine$^{SR}$ (0.1 to 0.27 mg/kg).

During the recovery period, sheep were connected to hemodynamic monitors, IV fluid resuscitated with lactated Ringer's solution, and provided with food and water. The vascular catheters and lines were continuously flushed with heparinized saline.

Baseline Variables: After 5 to 7 days of surgical recovery, baseline measurements of respiratory and hemodynamic variables were taken in awake, un-anesthetized sheep.

Baseline variables included the following:
Cardiopulmonary Hemodynamics:
  Heart rate;
  Mean arterial pressure;
  Cardiac output;
  Left atrial pressure;
  Central venous pressure;
  Pulmonary arterial pressure;
  Pulmonary artery occlusion pressure; and
  Calculated variables: cardiac index, systemic vascular and pulmonary arterial resistance index, pulmonary capillary pressure, and left and right ventricular stroke volume index.
  Core body temperature
Arterial and Venous Blood Gas Analysis, Complete Blood Cell Count:
  $PO_2$, $CO_2$, $SO_2$, hematocrit, hemoglobin, pH, electrolytes (Na, K, Ca, Cl), lactate, and glucose;
  Calculated variables—partial pressure of oxygen in arterial blood ($PaO_2$)/partial pressure of inspired oxygen ($FiO_2$) ratio and pulmonary shunt fraction
  Complete blood cell count.

Exclusion criteria. If any of following symptoms was present, sheep were removed from the study:
  $PaO_2$<90 mmHg at room air,
  Hematocrit <20%,
  Hemoglobin <7 g/dL,
  Core body temperature >40° C. (normal sheep body temperature was approximately 39.6° C.),
  White cells >10 k/µL.

Induction of ALI: Immediately prior to study initiation, sheep were subjected to ketamine anesthesia at 5 mg/kg, via IV injection, followed by a long-acting (72 h) buprenorphine analgesia at 0.1 mg/kg, via SC injection. A tracheostomy was performed, and anesthesia maintained using IV Propofol with initial bolus of 50 mg thereafter titrated to effect. Sheep were ventilated at a positive end-expiratory pressure (PEEP) of 5 cm $H_2O$, with a tidal volume (TV) 12 mL/kg. A Foley catheter was passed through the urethra to catheterize the bladder to allow for continuous urine collection for measurement of urine output. Animals were to receive a chest X-ray prior to chlorine exposure and prior to euthanasia (if applicable).

Injury was induced by endotracheal delivery of chlorine, at concentration of 210 ppm in air, for 30 min via a closed ventilatory circuit connected to the chlorine tank. The ventilator was set at 12 mL/kg of tidal volume, 5 cm $H_2O$ of PEEP, and 20 b/min of respiratory rate. The setting enabled comparable exposure among the animals.

The chlorine level of inhaled gas was certified as a premixed blend of chlorine and medical grade air supplied via the ventilator without dilution. The total flow of chlorine/air mixture was determined via a mass flow meter with stainless steel components placed immediately after the regulator. The chlorine tank was preheated (24 h) with electric warmer to 40° C. to properly mix the gas. During the 30-min injury period, blood gas analysis was performed every 10 minutes and cardiopulmonary variables were recorded. During the exposure, a possible chlorine leak was monitored at least by 2 monitors. The exposure was performed in a special room with negative pressure and toxic gas evacuation hood. At least 3 TICU personnel wearing designated PPE including respirator induced the exposure and provided care. After the 30-minute chlorine exposure, the sheep were ventilated with air (no chlorine) 10 minutes to flush out the chlorine residue from both sheep airways and the ventilatory circuits. Then, sheep were disconnected from the ventilator and transferred to the ICU station.

Post-injury monitoring: After the transferring the sheep to the ICU station, sheep were placed on a mechanical ventilator (Avea APVcmv mode: RR 20 b/m, TV 12 mL/kg, PEEP 5 cm $H_2O$), connected to the hemodynamic monitors and monitored for 48 hrs in a conscious state. Sheep were humanely euthanized at 48 hrs after the injury under deep anesthesia and analgesia. If during the study, one of following occurred, and not reversed for 1 h despite resuscitation, sheep were humanely euthanized.

$PaO_2/FiO_2$ ratio <50 mmHg
$PaCO_2$>90 mmHg
MAP <50 mmHg.

Grouping and treatment: After the injury, sheep were randomly assigned to one of following 4 groups:
1. Negative Control: exposed to chlorine, treated with equal amount of vehicle (5% Kolliphor EL and 50% propylene glycol and saline);
2. Positive Control: exposed to chlorine, treated with PDE4 inhibitor (rolipram, 3 mg).
3. MN-166 (high dose): exposed to chlorine, treated with MN-166 high dose (20 mg); and
4. MN-166 (low dose): exposed to chlorine, treated with MN-166 low dose (10 mg).

Each sheep received a final volume of 20 mL over a 30-min infusion.

Each group included 8 sheep. The total number of sheep for entire study was 36 including 1 sheep per group for possible technical errors (36=8 sheep per group×4 groups+4 sheep (1 sheep per group) for experimental failure/errors). During the study period, sheep were fluid resuscitated with lactated Ringer's solution 2 mL/kg/h.

Endpoints. Following treatment, study assessments were performed in the same manner as baseline variables. A description of each assessment is provided below.
1. Pulmonary function: was assessed by 1) intermittent (every 6 h) arterial and venous blood gas analyses, which include arterial and venous blood $PaO_2$, $CO_2$, $SO_2$, base excess, pH, and $SO_2$. Additionally, arterial hematocrit, hemoglobin, electrolytes, glucose, and lactate were measured every 6 h. $PaO_2/FiO_2$ ratio were calculated to determine severity of ARDS. Bilateral pulmonary infiltration was confirmed by chest X-ray taken at the end of study. The chest X-ray was taken before the injury as well. Pulmonary shunt fraction was calculated by a standard formula; and 2) pulmonary mechanics i.e., lung compliance, airway peak and pause pressures and dead space were taken every 6 h from ventilator readouts.
2. Lung injury and edema formation was assessed postmortem by histology (alveolar and interstitial edema), and lung water content (wet-to-dry weight ratio) in addition to chest X-ray. Lung tissue histology also included parenchymal congestion, hemorrhage, accumulation of inflammatory cells, atelectasis, and airway epithelia exfoliation.
3. Cardiopulmonary hemodynamics was continuously monitored, and variables indicated in baseline were recorded every 6 h.
4. Systemic vascular permeability was assessed by determination of accumulated net fluid balance for 48 h (fluid in and urinary output measured every 6 h), plasma protein, fluid accumulation in body cavities (thoracic and abdominal).
5. Complete peripheral blood cell count was determined every 6 h.

Sampling: 1) Arterial blood was taken every 6 h first 24 h and every 12 h at second 24 h, and aliquots of plasma and serum were stored at −20° C. for future assessments; 2) aliquots of urine were taken at indicated time points and stored in at −20° C.; 3) Bronchoalveolar lavage was performed at the end of study and aliquots were frozen and stored at −20° C.

Necropsy: At 48 h post Cl2 exposure (or upon reaching euthanasia criteria [see above]), sheep were exsanguinated under anesthesia by IV administration of an infusion of 100 mg Xylazine, 1500 mg ketamine, and 0.3 mg fast acting Buprenorphine consistent with the recommendations of the Panel on Euthanasia of the American Veterinary Medical Association. Just prior to necropsy a thoracic X-ray was performed, if applicable, using portable digital X-ray machine.

Postmortem Sampling: Following euthanasia, the heart and entire lung and upper respiratory tract were excised. Organ weights and images of heart and lung were taken. Aliquots of trachea, bronchi, lung parenchyma, heart, liver, and kidney were stored as frozen at −80° C. and fixed in formalin. The volume of thoracic and abdominal fluid was measured, if present, and total protein was measured. Aliquots of lung tissue were also taken for measurement of lung wet-to dry weight ratio.

Statistical analysis: Statistical analysis was performed using GraphPad Prism 8 software with two-or-one way ANOVA and T-test when applicable.

Interim Study Results: $PaO_2/FiO_2$ ratios were calculated at each time-point after chlorine exposure. $PaO_2/FiO_2$ results (mm Hg) for 4 animals [negative control (control-N), positive control (control-P), High MN-166, Low MN-166] at various time-points are shown in the table below and in the FIGURE.

| Time-point (h) (post-chlorine gas exposure) | Control-N (vehicle) | Control-P (rolipram, 3 mg) | High MN-166 (MN-166, 20 mg) | Low MN-166 (MN-166, 10 mg) |
| --- | --- | --- | --- | --- |
| 0 | 560.5 | | 650 | 507.1 |
| 1 | 103.2 | 522.9 | 415.1 | 295.8 |
| 3 | 121.4 | 315.3 | 331.7 | 292.6 |
| 6 | 108.8 | 391.6 | 329 | 368.5 |
| 12 | 79.3 | 322.7 | 461.3 | 329.3 |
| 18 | 84.5 | 235.8 | 313.2 | 340 |
| 24 | 91.3 | 144.5 | 392.2 | 382.3 |
| 30 | 110.7 | 84.6 | 434.2 | 381.2 |
| 36 | 128.1 | 97.9 | 409.6 | 365.8 |
| 42 | 177.1 | 102.7 | 466.7 | 335.6 |
| 48 | 123.2 | 59 | 445.7 | 339.3 |

The worsening of $PaO_2/FiO_2$ ratios was observed after chlorine exposure in all groups by hour 3 post-chlorine exposure. $PaO_2/FiO_2$ remained less than 200 mm Hg (moderate ARDS) or less than 100 mm Hg (severe ARDS) with all time-points in the negative control animal treated with vehicle only. $PaO_2/FiO_2$ remained less than 300 mm Hg (mild ARDS) at the 18 hour time-point and less than 200 mm Hg or less than 100 mm Hg after the 24-hour time-point post-chlorine gas exposure in the positive control animal (treated with rolipram, 3 mg). The animal treated with low dose MN-166 (10 mg) improved $PaO_2/FiO_2$ above 300 mm Hg after the 6-hour time-point post chlorine gas exposure and remained above 300 mm Hg. $PaO_2/FiO_2$ values for the animal treated with high dose MN-166 (20 mg) never decreased below 300 mm Hg in all time-points and increased to above 400 mm Hg by the 30-hour time-point.

Example 4: Administration of Ibudilast to Human Patient with Chemical-Induced Lung Injury A human patient suffering from symptoms (e.g., one or more of chemical burns, pulmonary edema, laryngeal edema, lung tissue apoptosis, pneumonia, pneumonitis, bronchitis, bronchiolitis, fibrosis, acute respiratory distress syndrome, or respiratory tract spasm) from chemical-induced lung injury due to chlorine, sulfur mustard gas, phosgene, Lewisite, hydrogen chloride, sulfur dioxide, hydrogen sulfide, nitrogen dioxide, ammonia, hydrofluoric acid, ozone, methyl isocyanate, or a combination of two or more thereof, is administered up to 100 mg of ibudilast.

Response to the ibudilast is assessed by respiratory rate measurement, blood oxygen level measurement (i.e., by pulse oximeter), dyspnea scale (e.g., modified medical research council dyspnea score), pulmonary function test (i.e., by spirometer), chest imaging study (i.e., chest X ray, chest CT), or any combination of two or more thereof.

Certain Embodiments

Embodiment 1. A method of treating chemical-induced lung injury in a subject in need thereof, the method comprising administering to the subject a therapeutically effective amount of ibudilast, or a pharmaceutical salt thereof.

Embodiment 2. The method of Embodiment 1, wherein the lung injury is induced by a chemical selected from chlorine, sulfur mustard gas, phosgene, Lewisite, hydrogen chloride, sulfur dioxide, hydrogen sulfide, nitrogen dioxide, ammonia, hydrofluoric acid, ozone, methyl isocyanate, and a combination of two or more thereof.

Embodiment 3. The method of Embodiment 1 or Embodiment 2, wherein the lung injury comprises chemical burns, pulmonary edema, laryngeal edema, lung tissue apoptosis, pneumonia, pneumonitis, bronchitis, bronchiolitis, fibrosis, acute respiratory distress syndrome, respiratory tract spasm, or a combination of two or more thereof.

Embodiment 4. The method of any one of Embodiments 1-3, wherein ibudilast, or the pharmaceutically acceptable salt thereof, is administered orally.

Embodiment 5. The method of any one of Embodiments 1-3, wherein ibudilast, or the pharmaceutically acceptable salt thereof, is administered intravenously.

Embodiment 6. The method of any one of Embodiments 1-3, wherein ibudilast, or the pharmaceutically acceptable salt thereof, is administered by subcutaneous injection.

Embodiment 7. The method of any one of Embodiments 1-3, wherein ibudilast, or the pharmaceutically acceptable salt thereof, is administered by intramuscular injection.

Embodiment 8. The method of any one of Embodiments 1-3, wherein ibudilast, or the pharmaceutically acceptable salt thereof, is administered by inhalation.

Embodiment 9. The method of any one of Embodiments 1-8, wherein ibudilast, or the pharmaceutically acceptable salt thereof, is administered for 1, 2, 3, 4, 5, 6, 7, 8, 9, or 10 days, or more.

Embodiment 10. The method of any one of Embodiments 1-8, wherein ibudilast, or the pharmaceutically acceptable salt thereof, is administered for at least 3 months.

Embodiment 11. The method of any one of Embodiments 1-10, wherein ibudilast, or the pharmaceutically acceptable salt thereof, is administered at least once daily.

Embodiment 12. The method of any one of Embodiments 1-10, wherein ibudilast, or the pharmaceutically acceptable salt thereof, is administered twice daily.

Embodiment 13. The method of any one of Embodiments 1-12, wherein the therapeutically effective amount of ibudilast, or the pharmaceutically acceptable salt thereof, is from 0.1 mg to 720 mg per day.

Embodiment 14. The method of any one of Embodiments 1-12, wherein the therapeutically effective amount of ibudilast, or the pharmaceutically acceptable salt thereof, is from 30 mg to 200 mg per day.

Embodiment 15. The method of any one of Embodiments 1-12, wherein the therapeutically effective amount of ibudilast, or the pharmaceutically acceptable salt thereof, is 40 mg to 600 mg daily.

Embodiment 16. The method of any one of Embodiments 1-12, wherein the therapeutically effective amount of ibudilast, or the pharmaceutically acceptable salt thereof, is 100 mg to 480 mg daily.

Embodiment 17. The method of any one of Embodiments 1-12, wherein the therapeutically effective amount of ibudilast, or the pharmaceutically acceptable salt thereof, is selected from the group consisting of 30 mg/day, 60 mg/day, 90 mg/day, 100 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

Embodiment 18. The method of any one of Embodiments 1-17, wherein the therapeutically effective amount is administered as a single dose or is divided into two, three, or four doses.

Embodiment 19. The method of any one of Embodiments 1-17, wherein ibudilast is administered continually.

Embodiment 20. The method of any one of Embodiments 1-19, wherein ibudilast, or the pharmaceutically acceptable salt thereof, is the only active agent administered to the patient.

Embodiment 21. The method of any one of Embodiments 1-19, wherein ibudilast, or the pharmaceutically acceptable salt thereof, is administered to the patient with at least one other active agent.

Embodiment 22. The method of Embodiment 21, wherein the at least one other active agent comprises a corticosteroid.

EQUIVALENTS

It should be understood that although the present disclosure has been specifically disclosed by certain embodiments and optional features, modification, improvement and variation of the disclosures embodied disclosed herein may be resorted to by those skilled in the art, and that such modifications, improvements and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

What is claimed is:

1. A method of treating chlorine-induced acute lung injury in a subject in need thereof, the method comprising administering to the subject a therapeutically effective amount of ibudilast, or a pharmaceutical salt thereof, wherein the lung injury is acute respiratory distress syndrome.

2. The method of claim 1, wherein ibudilast, or the pharmaceutically acceptable salt thereof, is administered orally.

3. The method of claim 1, wherein ibudilast, or the pharmaceutically acceptable salt thereof, is administered intravenously.

4. The method of claim 1, wherein ibudilast, or the pharmaceutically acceptable salt thereof, is administered by subcutaneous injection.

5. The method of claim 1, wherein ibudilast, or the pharmaceutically acceptable salt thereof, is administered by intramuscular injection.

6. The method of claim 1, wherein ibudilast, or the pharmaceutically acceptable salt thereof, is administered by inhalation.

7. The method of claim 1, wherein ibudilast, or the pharmaceutically acceptable salt thereof, is administered for 1, 2, 3, 4, 5, 6, 7, 8, 9, or 10 days, or more.

8. The method of claim 1, wherein ibudilast, or the pharmaceutically acceptable salt thereof, is administered for at least 3 months.

9. The method of claim 1, wherein ibudilast, or the pharmaceutically acceptable salt thereof, is administered at least once daily.

10. The method of claim 1, wherein ibudilast, or the pharmaceutically acceptable salt thereof, is administered twice daily.

11. The method of claim 1, wherein the therapeutically effective amount of ibudilast, or the pharmaceutically acceptable salt thereof, is from 0.1 mg to 720 mg per day.

12. The method of claim 1, wherein the therapeutically effective amount of ibudilast, or the pharmaceutically acceptable salt thereof, is from 30 mg to 200 mg per day.

13. The method of claim 1, wherein the therapeutically effective amount of ibudilast, or the pharmaceutically acceptable salt thereof, is 100 mg to 480 mg daily.

14. The method of claim 1, wherein the therapeutically effective amount is administered as a single dose or is divided into two, three, or four doses.

15. The method of claim 1, wherein ibudilast is administered continually.

16. The method of claim 1, wherein ibudilast, or the pharmaceutically acceptable salt thereof, is the only active agent administered to the patient.

17. The method of claim 1, wherein ibudilast, or the pharmaceutically acceptable salt thereof, is administered to the patient with at least one other active agent.

18. The method of claim 17, wherein the at least one other active agent comprises a corticosteroid.

* * * * *

UNITED STATES PATENT AND TRADEMARK OFFICE
CERTIFICATE OF CORRECTION

| | |
|---|---|
| PATENT NO. | : 11,925,625 B2 |
| APPLICATION NO. | : 17/586630 |
| DATED | : March 12, 2024 |
| INVENTOR(S) | : Kazuko Matsuda and Federico Carlos Aréjola Gaeta |

It is certified that error appears in the above-identified patent and that said Letters Patent is hereby corrected as shown below:

In the Claims

Column 25, Claim 1, Line 15, "or a pharmaceutical salt thereof," should be -- or a pharmaceutically acceptable salt thereof, --

Signed and Sealed this
Twenty-third Day of April, 2024

Katherine Kelly Vidal
*Director of the United States Patent and Trademark Office*